US011154631B2

(12) United States Patent
Dayton

(10) Patent No.: US 11,154,631 B2
(45) Date of Patent: Oct. 26, 2021

(54) COMPUTER OBJECT DECONTAMINATION APPARATUS AND METHOD

(71) Applicant: Diversey, Inc., Fort Mill, SC (US)

(72) Inventor: Roderick M. Dayton, Charlotte, NC (US)

(73) Assignee: Diversey, Inc., Fort Mill, SC (US)

( * ) Notice: Subject to any disclaimer, the term of this patent is extended or adjusted under 35 U.S.C. 154(b) by 0 days.

(21) Appl. No.: 16/495,938

(22) PCT Filed: Mar. 21, 2018

(86) PCT No.: PCT/US2018/023459
§ 371 (c)(1),
(2) Date: Sep. 20, 2019

(87) PCT Pub. No.: WO2018/175514
PCT Pub. Date: Sep. 27, 2018

(65) Prior Publication Data
US 2020/0138995 A1 May 7, 2020

Related U.S. Application Data

(60) Provisional application No. 62/474,364, filed on Mar. 21, 2017.

(51) Int. Cl.
*A61L 2/24* (2006.01)
*A61L 2/10* (2006.01)

(52) U.S. Cl.
CPC .................. *A61L 2/24* (2013.01); *A61L 2/10* (2013.01); *A61L 2202/11* (2013.01); *A61L 2202/14* (2013.01)

(58) Field of Classification Search
CPC .......... A61L 2/10; A61L 2/24; A61L 2202/14; A61L 2202/16; A61L 2202/25;
(Continued)

(56) References Cited

U.S. PATENT DOCUMENTS

2007/0195550 A1   8/2007  Tsai
2008/0067417 A1*  3/2008  Lane ........................ A61L 2/24
                                                        250/455.11
(Continued)

FOREIGN PATENT DOCUMENTS

GB    2528323 A      1/2016
WO    2008096123 A1  8/2008

OTHER PUBLICATIONS

EP International Search Report and Written Opinion for PCT/US2018/023459 dated Oct. 12, 2018.

*Primary Examiner* — David A Vanore
(74) *Attorney, Agent, or Firm* — Kilpatrick Townsend & Stockton LLP

(57) ABSTRACT

Provided is a decontamination apparatus for rendering an object pathogen reduced. The decontamination apparatus includes a frame to be positioned in suitable proximity to the object to enable the decontamination apparatus to perform a decontamination process that achieves at least a predetermined minimum level of pathogen reduction on the computer peripheral. A light source coupled to the frame to be transported along a decontamination path emits ultraviolet light suitable to deactivate at least a portion of a pathogen population on the computer peripheral. A shield interferes with transmission of the ultraviolet light in directions generally away from the computer peripheral, and a controller operates the light source and transports the light source along the decontamination path during the decontamination process.

20 Claims, 7 Drawing Sheets

(58) Field of Classification Search
CPC .. A61L 2209/111; A61L 9/20; A61L 2202/11; H05B 31/50; H05B 45/10; H05B 45/14; H05B 45/50; H05B 47/19; A61N 2005/0652; A61N 5/0624
USPC .............................. 250/454.11, 455.11, 492.1
See application file for complete search history.

(56) References Cited

U.S. PATENT DOCUMENTS

| | | | |
|---|---|---|---|
| 2008/0067418 A1* | 3/2008 | Ross ......................... | A61L 2/10 250/455.11 |
| 2009/0218512 A1* | 9/2009 | Ranta ........................ | A61L 2/10 250/455.11 |
| 2010/0127189 A1* | 5/2010 | Boyarsky .................. | A61L 2/24 250/492.2 |
| 2011/0095206 A1 | 4/2011 | Noto | |
| 2015/0090904 A1* | 4/2015 | Cole ......................... | A61L 2/10 250/492.1 |
| 2016/0074545 A1* | 3/2016 | Kim ......................... | H04R 1/12 250/455.11 |
| 2018/0272015 A1* | 9/2018 | Pangan, Jr. ............... | A61L 2/24 |

\* cited by examiner

COMPUTER OBJECT DECONTAMINATION APPARATUS AND METHOD

BACKGROUND OF THE INVENTION

1. Field of the Invention

This application relates generally to a decontamination apparatus and method and, more specifically, to a method and apparatus for decontaminating exposed surfaces of a computer object.

2. Description of Related Art

Walk-in healthcare clinics are growing in popularity as destinations for seeking medical treatment of routine medical conditions without the need to schedule an appointment. The clinics can often diagnose illnesses that can be treated with an antibiotic that can be filled on sight, or recommend more-comprehensive medical attention when warranted. To make the cost of their services affordable, however, such clinics will keep staff levels at a minimum and use self-serve kiosks to allow patients to register for treatment upon arriving at the clinic. As the advantages resulting from using self-serve kiosks become more apparent, the kiosks are beginning to gain widespread acceptance in full-service medical facilities and even reception areas in buildings of other industries.

The self-serve kiosks generally have a computer-controlled display that is touch sensitive that interfaces with the arriving patients. Patients can register by tapping various soft keys displayed as part of a graphical user interface that walks the patients through a menu of questions and forms. However, since these patients are at the clinic to seek medical treatment of an illness, pathogens may be introduced to the touch-screen display during the registration process. Subsequent users may further contaminate the touch-screen display, but may also be infected by the pathogen introduced by previous users resulting in the spread of a contagious condition.

The touch-screen display of a self-service kiosk is an example of a publicly-accessible computer object such as a peripheral, for example, that has the potential to spread infectious organisms. But this potential exists for computer objects that may not be publicly-accessible. Physicians, nurses and other staff members at hospitals and other healthcare facilities will often interact with sick patients, and then enter data into an electronic health record via a computer keyboard, computer mouse or other interface device. Often, the use of such computer objects will occur during or immediately after interactions with patients, possibly resulting in contamination of the computer keyboard, for example, with pathogens spread from interactions between the staff member using the keyboard and the patient. Subsequent users of the keyboard, and even the same user of the keyboard after washing, may become infected by viable pathogens transmitted from the keyboard.

BRIEF DESCRIPTION OF SEVERAL VIEWS OF THE DRAWING

The invention may take physical form in certain parts and arrangement of parts, embodiments of which will be described in detail in this specification and illustrated in the accompanying drawings which form a part hereof and wherein.

DETAILED DESCRIPTION OF THE INVENTION

Figure 1:
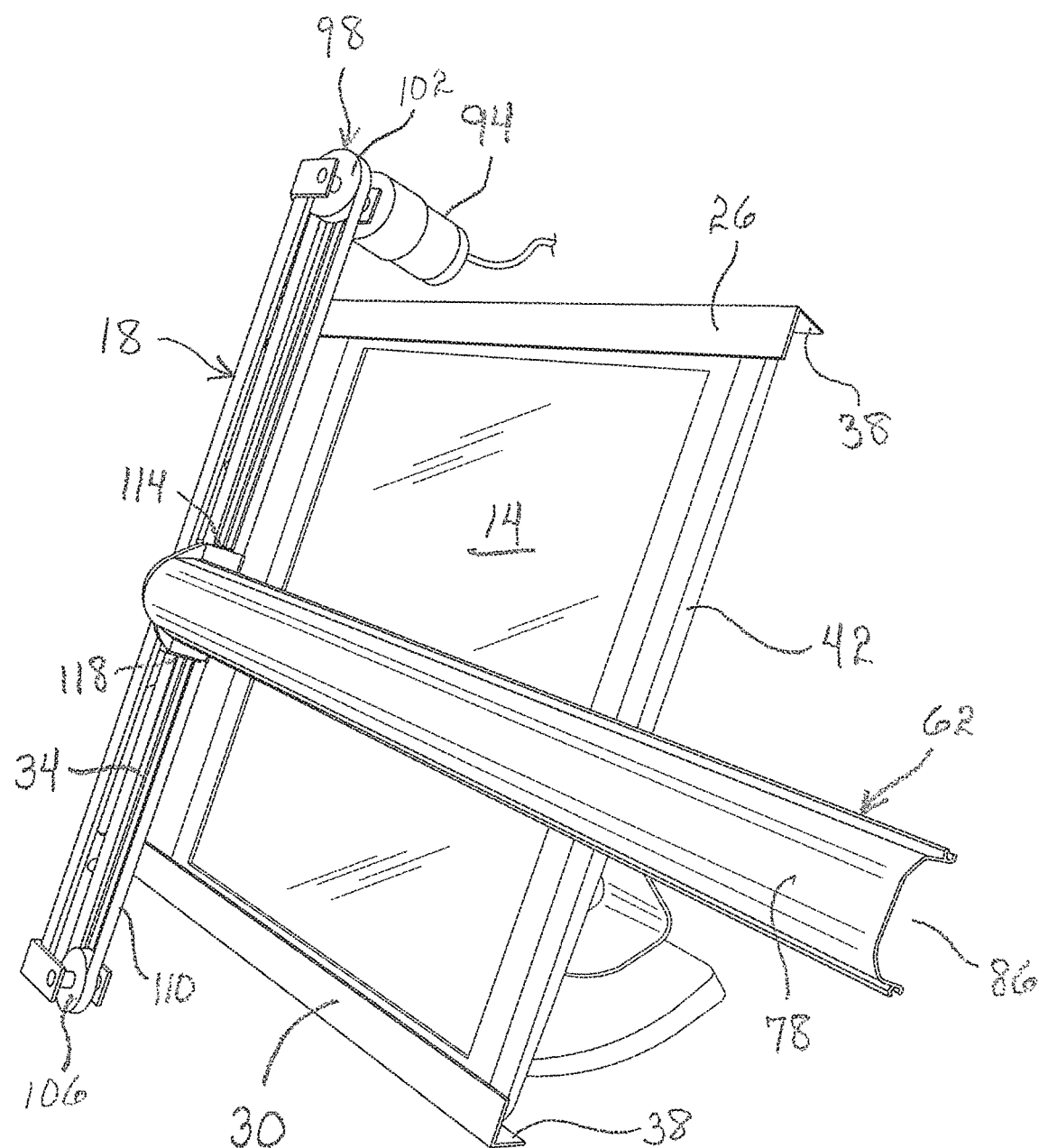
FIG. 1 is a perspective view showing an illustrative embodiment of a track installed on a touch-sensitive computer display, the track supporting an ultraviolet light source.

Certain terminology is used herein for convenience only and is not to be taken as a limitation on the present invention. Relative language used herein is best understood with reference to the drawings, in which like numerals are used to identify like or similar items. Further, in the drawings, certain features may be shown in somewhat schematic form.

The present application is directed toward a decontamination apparatus that, during a decontamination process initiated and controlled automatically, renders a computer object (e.g., keyboard, pointing mouse, etc.) or other object pathogen reduced. The decontamination apparatus includes a frame that is configured to be positioned adjacent to the computer object to be rendered pathogen reduced. When the decontamination apparatus is properly positioned, a light source that emits ultraviolet light or another decontamination source (e.g., a mister that emits a mist or fog formed from droplets of a liquid disinfectant) is activated by a controller. The controller also operates a drive system including a motor, actuator or other suitable prime mover to cause the light source or other source of a disinfectant to travel along a decontamination path, thereby exposing surfaces of the computer object and any pathogens supported on such surfaces to the ultraviolet light or disinfectant, rendering the computer object pathogen reduced. For embodiments that utilize ultraviolet light, a shield formed from a material opaque to ultraviolet light is provided to the light source to block ultraviolet light that would be emitted in a direction away from the computer object, thereby limiting the possibility of exposing a person to ultraviolet light during a decontamination process. For other embodiments that apply a liquid disinfectant as a mist or fog, the shield can be formed from any material, regardless of opacity, that blocks the flow of the mist or fog in directions other than toward the computer object. At least one sensor can be provided to sense movement or another quality indicative of the presence of a person within a defined distance of the decontamination apparatus, and transmit a signal to the controller which, in response to receiving this signal, terminates the emission of ultraviolet light or the liquid disinfectant. The controller can also optionally cause the source to be returned to a stowed location upon premature termination of the decontamination process in response to a signal from the one or more sensors.

Figure 4:
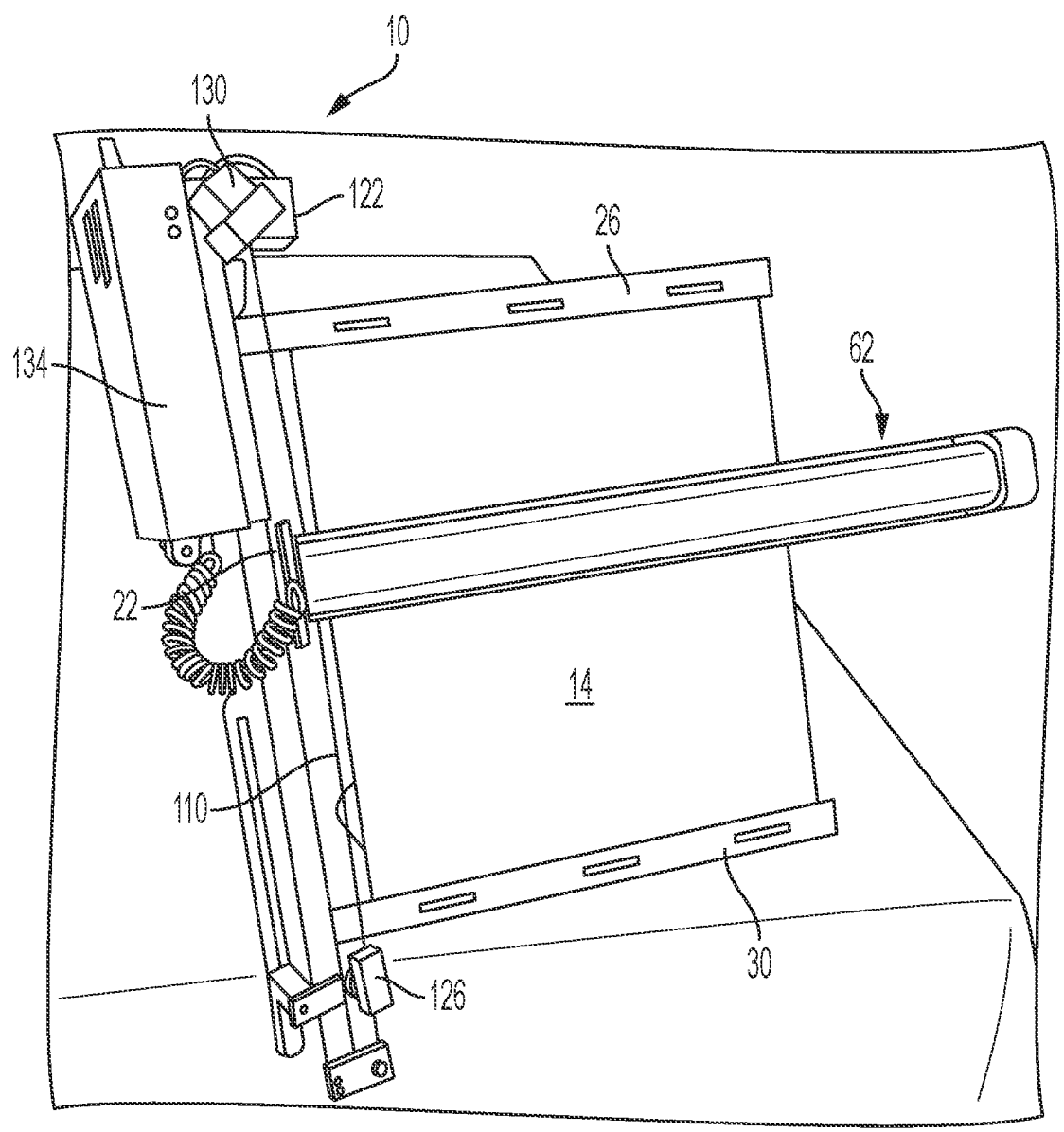
FIG. 4 is a perspective view showing an illustrative embodiment of a decontamination apparatus performing a decontamination process on a computer display.

More specifically, and with reference to the drawings, FIG. 4 shows an illustrative embodiment of a decontamination apparatus 10 installed on a computer display 14. The computer display 14 can be a touch-sensitive monitor that includes regions that can be tapped, swiped or otherwise manipulated by a user's finger(s) to input information or an instruction to the computer processor operatively connected to the computer display 14. Although the decontamination apparatus 10 is described in the present embodiment as a computer display 14, the object to be rendered pathogen reduced can be any object the decontamination apparatus 10 is configured to be secured to as described in detail below.

The embodiment of the decontamination apparatus 10 in FIG. 4 includes a frame 18 to be positioned in suitable proximity to the computer display 14 to enable the decontamination apparatus 10 to perform a decontamination process that achieves at least a predetermined minimum level of pathogen reduction on the computer display 14. Shown clearly in FIGS. 1 and 2, a pair of opposing rails 26, 30 are separated from each other by an adjustable distance along a track region 34 of the frame 18. Each rail 26, 30 can be formed of angle iron having a generally "L" shaped cross section, for example. The angled portion 38 of each rail 26, 30 extending in a depthwise direction of the computer display 14 can optionally be provided with padding that is disposed between the angled portion 38 of each rail 26, 30 and a portion of the frame 42 of the computer display 14 once the decontamination apparatus 10 is installed. According to alternate embodiments, each rail 26, 30 can be configured to cooperate with a mating portion of the specific computer display 14 or other object to be rendered pathogen reduced.

One of the rails 26 can be coupled to the track region 34 at a fixed location while the other rail 30 can be adjustably coupled to the track region 34. For example, the adjustable rail 30 can be slide along the track region 34 to be infinitely adjustable along the length of at least a portion of the track region 34, and then secured in place once the desired spacing from the opposite rail 26 has been achieved. A set screw, quick release camming mechanism, or any other releasable fastener can be used to secure the adjustable rail 30 to the track region 34 once the desired spacing has been established. Although the adjustable rail 30 in the example above is the lower rail 30 as shown in FIGS. 1-4, the rail 26 arranged above the rail 30 in those drawings can be made adjustable in addition to, or instead of rail 30. According to other embodiments, each of the plurality of rails 26, 30 can be made adjustable relative to the track region 34.

To install the present embodiment of the decontamination apparatus 10 on the computer display 14 and thereby position the frame 18 adjacent to the computer display 14 for performing the decontamination process, one or both of the rails 26, 30 can be adjusted along the track region 34 so the full height of the computer display 14 can be received therebetween. The at least one adjustable rail 30 can then be adjusted toward the other rail 26, or the rails 26, 30 can be adjusted toward each other, so the spacing between the rails 26, 30 is reduced to apply a compressive force along the height dimension of the computer display 14, which is a vertical direction in the drawings. The compressive force exerted on the computer display 14 by the rails 26, 30 interferes with removal of the decontamination apparatus 10 from the computer display 14 until the rails 26, 30 are again separated from each other a distance greater than the full height of the computer display 14.

Figure 3:
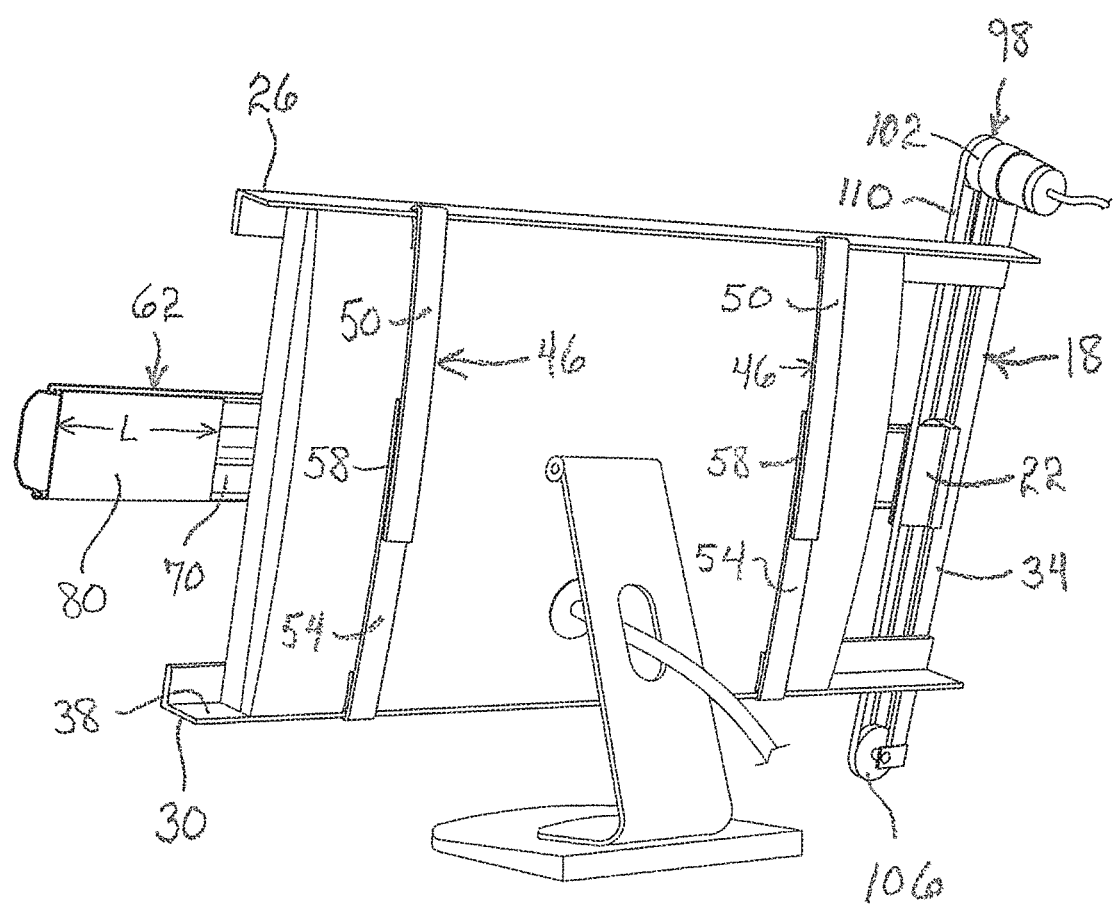
FIG. 3 is a rear perspective view of a track supporting an ultraviolet light installed on a computer display, the ultraviolet light source including a customizable shield interfering with transmission of ultraviolet light toward into a space behind the computer display.

To further secure the decontamination apparatus 10 to the computer display 14, embodiments of the decontamination apparatus 10 can include at least one, and optionally a plurality of straps 46 that extend across a rear surface of the computer display 14, between the rails 26, 30, as shown in FIG. 3. Each strap 46 can include a plurality of segments 50, 54. Upper segment 50 can extend downwardly from the rail 26, and lower segment can extend upwardly from the opposite rail 30. A releasable fastener such as a hook-and-loop system 58, tri-glide buckle, etc., that allows the effective length of the straps 46 to be adjusted to approximately match the distance separating the rails 26, 30. Thus, the straps 46 can reinforce the compressive force exerted by the rails 26, 30 on the computer display 14, and interfere with unintended separation of the rails 26, 30.

The track region 34 of the frame 18 supports a coupler 22 that receives the light source 62 (FIGS. 1, 3 and 4) that emits ultraviolet light onto a display region of the computer display 14. The display region of the computer display 14 is operable to present the graphical user interface to be manipulated by a user by touching the display region. As shown in FIG. 2, the coupler 22 includes an electrical connector 66 that cooperates with a compatible connector provided to the light source 62 to supply electric energy used to illuminate one or a plurality of ultraviolet bulbs 70 (FIG. 3) provided to the light source 62. A hub portion 74 of the coupler (FIG. 2) can provide a mechanical attachment point of the light source 62 to the coupler 22, supporting an arcuate shield 78.

Although a light source 62 is described as being coupled to the track region 34 by the coupler 22, sources of a suitable disinfecting agent other than ultraviolet light are also within the scope of the present disclosure. For example, a mister nozzle that emits a liquid disinfecting agent in small droplets forming a mist, fog, vapor or aerosol, for example, instead of the light source 62, can be coupled to the track region 34 by the coupler 22. An example of a suitable liquid disinfectant is a phosphate-free, pH-neutral composition that includes at least one of: an alcohol ethoxylate, n-alkyl dimethyl benzyl ammonium chloride, a salt of ethylenediaminetetraacetic acid, dioctyl dimethyl ammonium chloride, ethyl alcohol, accelerated hydrogen peroxide, hypochlorous acid, etc., that meets hospital-grade standards for disinfectants. One or more of the foregoing components can be present in a weight percent from about 1 wt % to about 3 wt %, or optionally from about 0.1 wt % to about 1 wt %. However, for the sake of clearly describing the present technology, illustrative embodiments including the light source 62 that emits ultraviolet light as the source of the disinfectant is described hereinafter.

The ultraviolet bulb(s) 70 can emit ultraviolet-C ("UVC") light, having a wavelength within a range from approximately 10 nm to approximately 400 nm. The ultraviolet bulb(s) 70 can remain active, emitting UVC light throughout their movement along the computer display 14 during the decontamination process, or they can be occasionally deactivated and reactivated as desired without departing from the scope of this disclosure.

UVC light deactivates pathogens to interfere with their ability to viably reproduce as required to cause a growing or otherwise worsening infection. So, for the computer display or other object to be rendered "pathogen reduced", at least a portion, optionally less than all, of a biologically-active contagion present on the exposed surface of the object exposed to the UVC light must be deactivated. For instance, rendering objects on the computer display 14 pathogen reduced does not necessarily require that object to be made 100% sterile, free of any and all biologically-active organisms that can viably infect a human being. Instead, being rendered pathogen reduced requires a lower level of biologically-active contagions viable to cause an infection remaining on the surface of the objects after performance of the decontamination process herein to be present than existed on the surface of the object prior to performance of the decontamination process. Also, deactivation of the biologically-active contagions can include killing live contagions, or at least neutralizing their ability (e.g., rendering them no longer viable) to reproduce to an extent that results in an infection in a human exposed to the deactivated contagions.

According to other embodiments, decontaminated surfaces can be required to possess a lower level of viable or otherwise biologically-active contagions than a threshold quantity permitted under U.S. Food and Drug Administration requirements on objects dedicated for use in a sterile field such as in an operating room during a surgical procedure. According to other embodiments, the decontamination process can be required to kill or otherwise deactivate at least 99% of all living or otherwise biologically-active contagions present on the exposed surfaces immediately prior to performance of the decontamination process to render those surfaces pathogen reduced.

According to yet other embodiments, achieving pathogen reduction amounting to a high-level disinfection of the surface of the computer device 14 utilizing the UVC light can involve deactivation of a suitable portion of the biologically-active contagions to achieve at least a 1 $\log_{10}$ reduction of viable contagions on the object that remain infectious (i.e., no more than 1/10th of the biologically-active contagions originally present remain active or infectious at a time when the decontamination process is completed). According to yet other embodiments, achieving high-level disinfection of the surface of the computer display 14 utilizing UVC light can involve deactivation of a suitable portion of the biologically-active contagions to achieve at least a 3 $\log_{10}$ reduction (i.e., 1/1,000th) of viable contagions originally present on that surface exposed to UVC light. According to yet other embodiments, achieving high-level disinfection of such a surface can involve deactivation of a suitable portion of the biologically-active contagions to achieve at least a 5 $\log_{10}$ reduction (i.e., 1/100,000th) of viable contagions thereon.

The shield 78 is arranged to interfere with transmission of ultraviolet light in directions generally away from the computer display 14 during the decontamination process, and into locations where a person standing in front of the computer display 14 may be exposed to the ultraviolet light. To limit the directions in which the ultraviolet light is emitted to generally toward the display region of the computer display 14, the arcuate shield can extend approximately 180 degrees, and optionally more, circumferentially about the ultraviolet bulb(s) 70. An inward-facing surface 82 (FIG. 3) of the shield 78 that opposes the ultraviolet bulb(s) 70 can optionally be provided with an anti-reflective material that interferes with reflection of the ultraviolet light emitted originally away from the computer display 14, back toward the display region of the computer display 14. For example, the inward-facing surface 82 can be provided with a matte-black coating such as paint.

According to other embodiments, however, the inward-facing surface 82 of the shield 78 can optionally be provided with a highly-reflective material. Such a material reflects ultraviolet light emitted originally away from the computer display 14 back toward the display region of the computer display 14. For such embodiments, the shield 78 can be supported by the coupler 22 so closely to the computer display 14 that small quantities of ultraviolet light can escape into the ambient environment of the decontamination apparatus 10. For example, a leading surface of the shield 78 ahead of the ultraviolet bulb(s) 70 and a trailing surface of the shield behind the bulb(s) 70 as the light source 62 travels along the decontamination path established by the track region 34 can optionally be separated from a surface of the display region of the computer display 14 by one (1 in.) inch or less. According to alternate embodiments, this separation can be three quarters (¾ in.) of an inch or less, or the separation can be one half (½ in.) of an inch or less, or the separation can be one quarter (¼ in.) of an inch or less, etc. According to alternate embodiments, there can be a flexible material (e.g., a cloth barrier, a barrier of bristles, etc.) extending between the leading and trailing edges of the shield 78 to prevent substantially all ultraviolet light from escaping the light source 62 into the ambient environment of the decontamination apparatus 10. To emit high-intensity UVC light onto the display region of the computer display 14, a perimeter of the ultraviolet bulb(s) can be arranged approximately even with the leading and trailing surfaces of the shield 78.

Because the computer display 14 may be located at the entrance to a waiting room, patients waiting to see a clinician may be seated behind the computer display 14. As shown in FIG. 3, the light source 62 has a length along a longitudinal axis of the light source 62 that causes a portion of the light source 62 to protrude beyond a lateral periphery of the computer display 14. To interfere with the emission of ultraviolet light by the protruding segment of the light source 62 beyond the computer device 14, a user customizable guard 80 can optionally be installed on the light source 62. The guard 80 is said to be user customizable in that the guard 80 can be cut to a desired length L to block ultraviolet light emitted by the protruding segment of the bulb(s) 70 into a region behind the computer display 14, but not significantly interfere with the emission of ultraviolet light onto the computer display 14. The guard 80 can include a plurality of lateral score marks that are formed occasionally (e.g., every eighth (⅛ in.) of an inch, every one quarter (¼ in.) of an inch, etc.) along the length of the guard 80. Thus, the decontamination apparatus 10 can be used with computer displays having various different widths.

Figure 8:
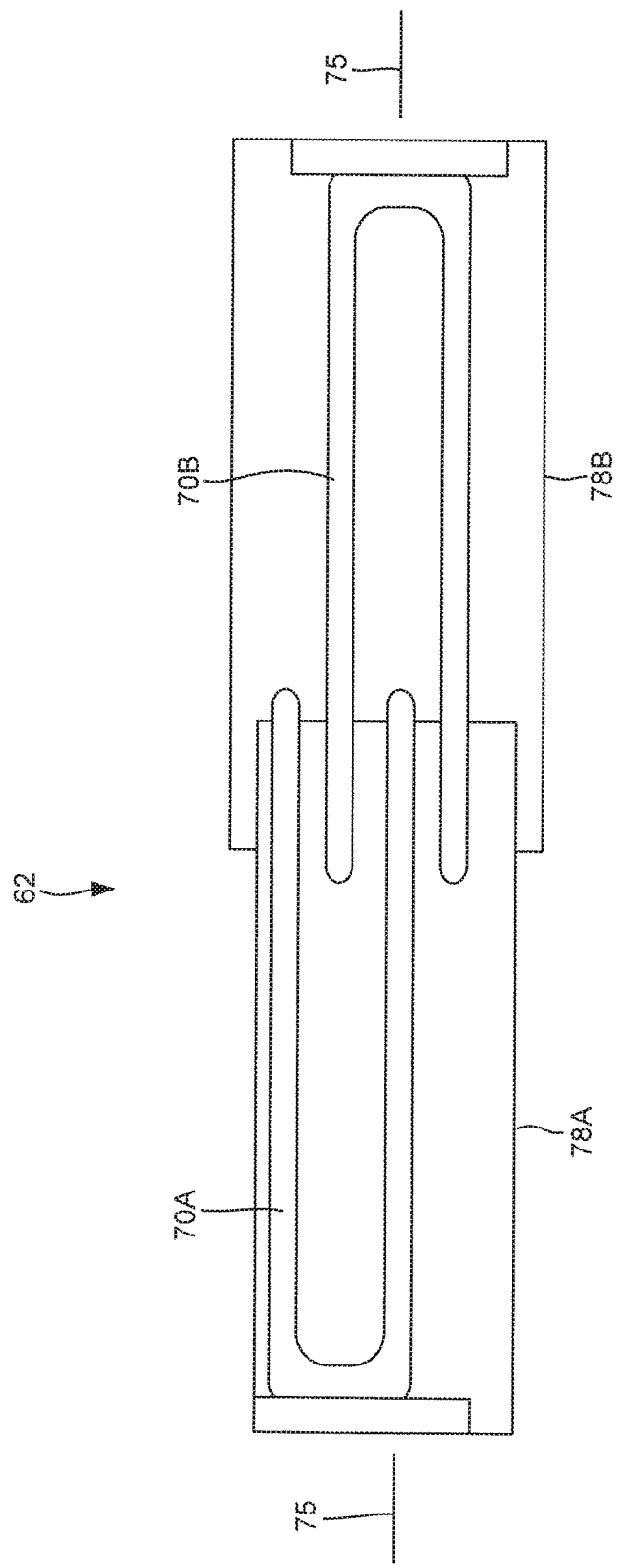
FIG. 8 is a schematic illustration of a light source having an adjustable length.

According to alternate embodiments, limiting the emission of UVC light and/or the application of the liquid disinfectant to the width or other dimension of the computer display can be achieved by limiting the length of the light source 62 or other source instead of installing the guard 80. For example, as shown in FIG. 8, the light source 62 can include a shield 78 that is broken into two telescopically-adjustable shield segments 78A, 78B. Likewise, instead of a single piece bulb 70 having a fixed length, the bulb 70 can include a plurality of short bulbs 70A, 70B that each have a length along a longitudinal axis 75 of the light source 62 that is approximately half the length of the light source 62, fully extended. However, there can be an overlap between the short bulbs as shown in FIG. 8, or a small gap between opposing terminal ends of the short bulbs 70A, 70B. As shown in FIG. 8, the light source 62 is fully extended, meaning the shield segments 78A, 78B are fully separated from each other to the maximum permissible extent. Even fully extended, there is a minor overlap between the shield segments 78A, 78B to protect against UVC light escaping between the shield segments 78A, 78B. Each shield segment 78A, 78B includes its own short bulb 70A, 70B, respectively. The short bulbs 70A, 70B are shown in the illustrated embodiment as being generally U-shaped, with the linear members interleaved, although any arrangement that would prevent a collision between the short bulbs 70A, 70B when the overall length of the light source 62 is shortened can be utilized. To shorten the overall length of the light source 62, at least one of the shield segments 78A, 78B is adjusted toward the other one of the shield segments 78A, 78B. The telescopic overlap between the shield segments 78A, 78B is greater when the overall length of the light source 62 is short than when the overall length of the light source 62 is long. In other words, shield segment 78B receives the shield segment 78A to a greater extent while the overall length of the light source 62 is short than when the light source 62 is fully extended. Similarly, the overlap between the interleaved linear segments of the short bulbs 70A, 70B also increases, thereby shortening the effective length of the bulb 70. By shortening the light source 62 to approximately match the width of the computer display 14, the protruding segment of the light source 62 can be avoided, along with the guard 80.

To further contain the ultraviolet light in an effort to prevent the ultraviolet light from being emitted into the ambient environment of the decontamination apparatus 10, an orientation of the shield 78 and/or the ultraviolet bulb(s) 70 relative to the display device or other object can be maintained throughout the decontamination process. As explained below, as the light source 62 is passed over the object being decontaminated, the opening 86 (FIG. 1) of the shield 78, which has a generally "U" shaped cross section, is maintained to face the computer display 14 at all times while traversing the computer display 14 during a decontamination process. Likewise, the orientation of the shield 78 is maintained so the opening 86 faces downward throughout the range of motion during decontamination of the keyboard 90 as described below with reference to FIGS. 5 and 6.

The coupler 22 that couples the light source 62 to the frame 18 rides along the track region 34 to be adjusted relative to the frame 18 and transported, along with the light source 62, along a decontamination path while the light source 26 is active during the decontamination process. For example, the coupler 22 can include a notch that receives a rail of the track region 34 to travel along a linear disinfection path during a decontamination process.

Figure 2:
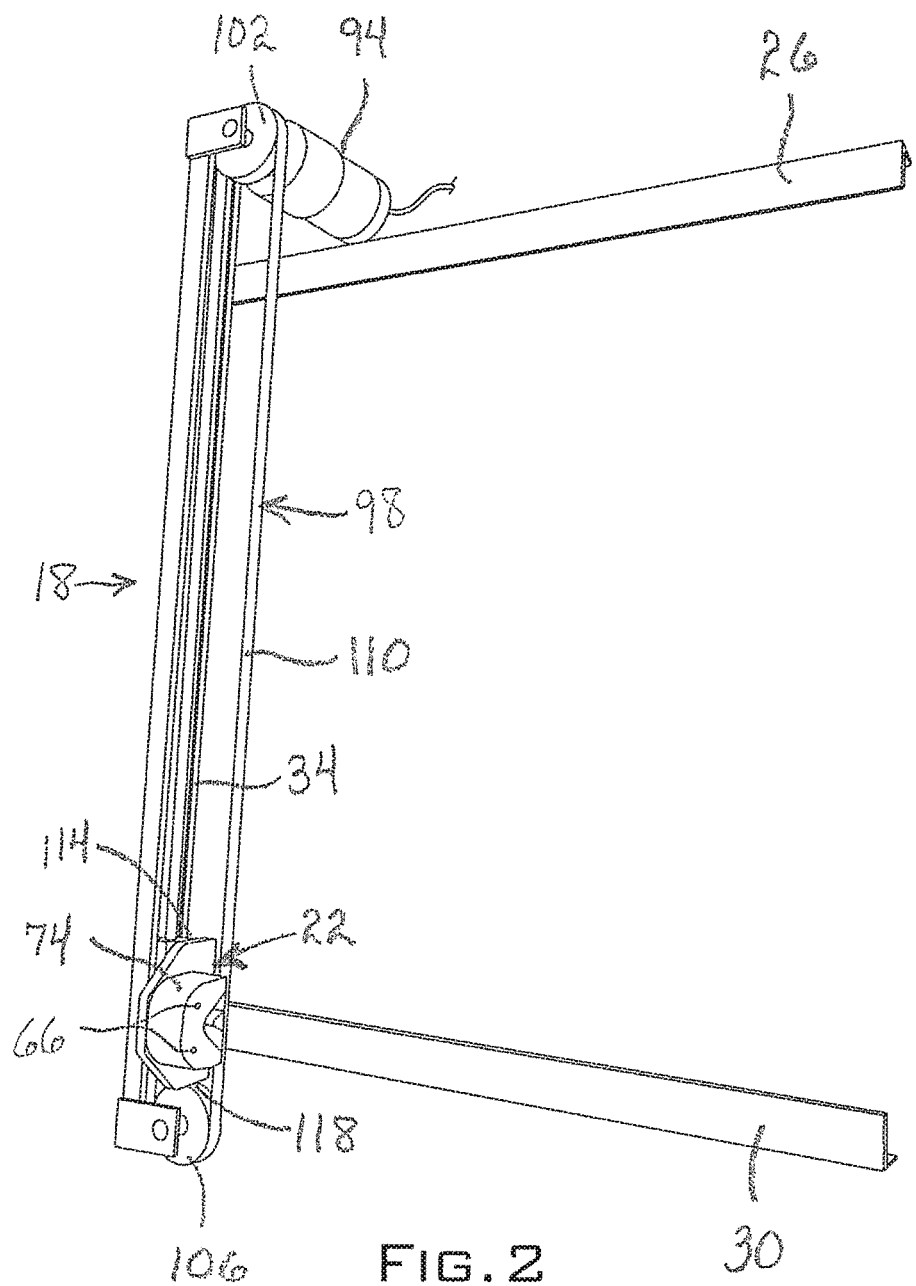
FIG. 2 is a perspective view of the track of FIG. 1 separated from the computer display.

A motor 94 can be supported by the frame 18, optionally adjacent to an end of the track region 34 as shown in FIGS. 1-3, to adjust the position of the coupler 22 supporting the light source 62 along the track region 34 during a decontamination process. A drivetrain 98 between the motor 94 and the coupler 22 transmits a force generated by the motor 94 to the coupler 22, thereby transporting the light source 62 along the decontamination path. For the embodiment shown in FIGS. 1-4, drivetrain is coupled to the frame 18 and includes a first sprocket 102 rotatably coupled to an end of the track region that is driven by the motor 94. A second sprocket 106 is coupled adjacent to an opposite end of the track region 34, and is freely rotatable. A belt 110 formed from a continuous loop of material extends about the sprockets 102, 106 to be coupled to opposite ends 114, 118 of the coupler 22, or to another portion of the coupler 22 such as a bottom region of the coupler 22 as shown in FIG. 2.

Rotation of the sprocket 102 by the motor 94 is transmitted to the other sprocket 106 by the belt 110, and causes the coupler 22 to travel along the track region 34.

One or more sensors can be provided to the decontamination apparatus 10 to affect movement of the light source 62, sense the presence of a person within a distance from the decontamination apparatus 10 and/or computer display 14, or a combination thereof. As shown in FIG. 4, the decontamination apparatus 10 includes a pair of limit switches 122, 126 adjacent to terminal ends of the decontamination path or track region 34. Each limit switch 122, 126 can be independently selected as a snap-action switch, but any suitable operator type can be employed, such as a lever, whiskers, a magnetic reed switch, an optical sensor, capacitive sensor, etc. Regardless of the type used, as the coupler 22 reaches the end of the permissible travel distance it makes contact with, or otherwise triggers the limit switch 126, causing the limit switch 126 to transmit a signal indicative of a travel limit being reached by the coupler 22. Similarly, as the coupler 22 returns to the permissible travel distance in the opposite direction it makes contact with, or otherwise triggers the limit switch 122, causing the limit switch 122 to transmit a signal indicative of the travel limit being reached by the coupler 22 in the opposite direction. The limit switches 122, 126 can each independently be established at a fixed location along the track region 34, or can be adjustable to allow an operator define different permissible travel limits along the track region 34. However, at least one of the limit switches 122, 126 can be positioned at a location along the length of the track region 34 where the light source 62 will not obstruct a view of the display region of the computer display 14 when stopped based on a signal transmitted by that limit switch. In other words, each limit switch 122, 126 used to stop movement of the light source 62 during a decontamination cycle can be position so the light source 62 stops outside the viewable display region of the computer display 14.

The embodiment of the decontamination apparatus 10 appearing in FIG. 4 also includes a proximity sensor 130 to sense the presence of a person within a distance from the decontamination apparatus 10 and/or computer display 14. The proximity sensor can utilize an optical motion sensor that monitors movement near the decontamination apparatus 10, a capacitive sensor that senses the presence of the person by sensing a change in sensed capacitance, or any other suitable sensor capable of sensing a person within a defined distance (e.g., up to five (5 ft.) feet, up to ten (10 ft.) feet, etc.) from the decontamination apparatus 10, and transmitting a signal indicative of the person's presence. Since the light source 62 emits light in a direction generally toward the computer display 14, the proximity sensor 130 can optionally be configured to include a single sensor, or optionally a sensor array that can sense the presence of a person within the defined distance in front of the computer display 14, or within the defined distance at any location within the full field, spanning the full 360 degrees about the computer display 14. Further, in view of the close proximity of the bulb(s) 70 to the computer display maintained over the entire decontamination path, the proximity sensor 130 can be configured to sense the presence of a person within a defined distance. This defined distance can be less than a permissible distance from the bulb(s) 70 where the person would receive an unacceptable does if the UVC light was emitted directly toward the person. In other words, the arrangement of the light source 62 on the frame 18 establishes a small space between the light source 62 and the computer display 14 to block enough of the UVC light during the decontamination process that a person could stand closer to the decontamination apparatus 10, while operational, than if the shield 78 was removed and the bulb(s) exposed. As a result, the proximity sensor 130 can allow a person to approach the decontamination apparatus 10 to a greater extent than would be permissible if the person was directly exposed to the bulb(s) 70. For example, the proximity sensor 130 can be configured to sense a person at a distance that is less than the distance to a wall, door or other partition of the room in which the computer display 14 is located, to transmit a signal that results in termination of a decontamination process. As a result, the decontamination apparatus 10 can perform a decontamination process involving emission of the UVC light or deposition of the liquid disinfectant onto the display region of the computer display 14 while there are occupants within the room provided with the computer display 14. So long as none of those occupants approaches the computer display 14 or otherwise enters the space within the defined distance from the computer display 14 as sensed by the proximity sensor 130, the decontamination apparatus 10 can perform a decontamination process to completion while the occupants are in the room.

According to alternate embodiments, the decontamination apparatus 10 can optionally communicate with the computer display 14 and/or other components (e.g., computer processor) of the computer terminal to which the computer display 14 is connected. For example, the decontamination apparatus 10 can include a sensor that is responsive to changes in the graphical user interface ("GUI") displayed by the computer display 14. As another example, the decontamination apparatus 10 can optionally be plugged into a port (e.g., USB port) provided to the computer terminal and/or the computer display 14 to sense activity involving the computer display 14. Regardless of the mechanism used, any activity involving the computer display 14 can be interpreted as a condition requiring deactivation of the light source 62 to avoid the possibility of exposing a user of the computer display 14 to ultraviolet light. Further, the light source 62, if not already located to avoid obscuring the view of the display region, can be repositioned outside of the perimeter of the display region.

Figure 7:
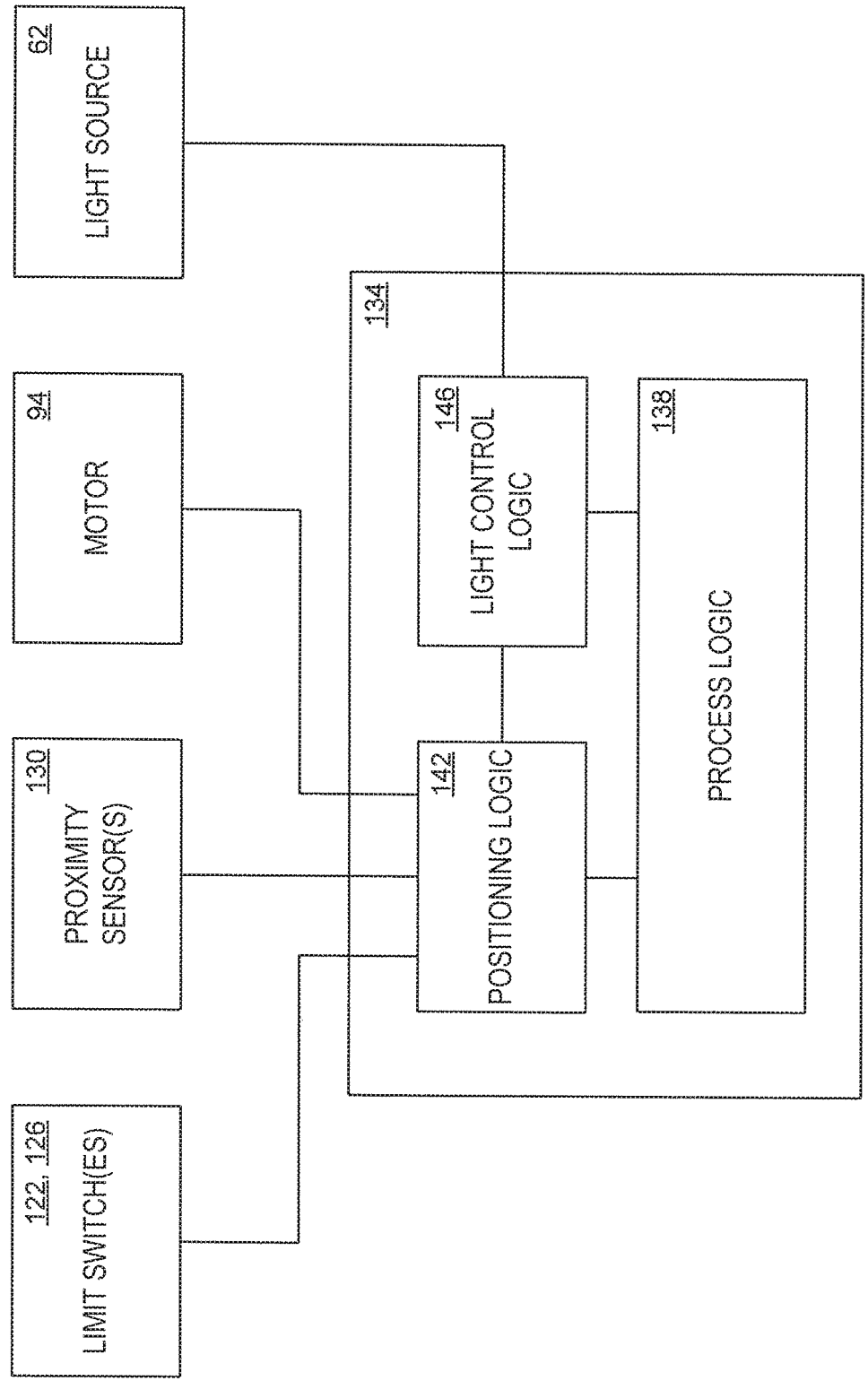
FIG. 7 is a block diagram schematically showing the components of a controller, and relationships between the controller components and a collection of sensors, a motor and a light source.

An illustrative embodiment of a controller 134 is shown in FIGS. 4 and 7 for controlling operation of the light source 62 and transportation of the light source 62 along the decontamination path during the decontamination process. The logic of the controller 134 can be implemented in hardware such as a computer processor programmed with instructions, a non-transitory computer-readable medium with stored instructions, firmware, and/or combinations thereof. Process logic 138 can store defined parameters of the decontamination processes to be performed by the decontamination apparatus 10. For example, the process logic 138 can store a parameter indicative of when a decontamination process is to commence. For example, such a parameter can be established to initiate a new decontamination process following a period of inactivity (e.g., nobody present within the defined distance from the computer display 14) of five (5 min.) minutes, or any other suitable period of inactivity. During the decontamination process, the light source 62 is transported along the track region 34 while the bulb(s) 70 are illuminated, thereby emitting UVC light that impinges on the computer display 14. Again, for the embodiments depositing a liquid disinfectant instead of (or in addition to) emitting UVC light, the mister is transported along the decontamination patch corresponding to the track region 34 to cover most of the exposed surface of the computer display 14.

The process logic 138 can establish the velocity at which the coupler 22, and accordingly the light source 62, travels along the length of the track region 34. The velocity can be established as one of a plurality of available velocities selected through user input, selected as a function of the intensity and/or quantity of the UVC bulb(s) 70, the distance separating the UVC bulb(s) 70 from the display region of the computer display 14, the level of pathogen reduction desired, or any other factor. The process logic 138 can also be configured to save data concerning the performance of decontamination processes for audit purposes. For example, the process logic 138 can cause the controller 134 to create entries in a non-transitory computer memory indicating whether a decontamination process was performed to completion, when the computer display 14 was last decontaminated by a decontamination process that was performed to completion, if a decontamination process was prematurely interrupted prior to completion based on a signal from the proximity sensor 130, etc.

Positioning logic 142 is configured to receive the signals transmitted by any of the limit switch(es) 122, 126 and proximity sensor(s) 130 provided to the decontamination apparatus 10. Responsive to such signals from the limit switches 122, 126, for example, the positioning logic 142 causes the controller 134 to determine that the light source 62 has reached the terminal travel limits of the track region 34 and change an operational direction of the motor 94, thereby causing the light source 62 to travel in the opposite direction. Responsive to receiving the signal from the proximity sensor 130, for example, the positioning logic 142 causes the controller 134 to determine that a person has approached the computer display 14 and relay that information to light control logic 146. The light control logic 146, in response to receiving the signal from the positioning logic 142, deactivates the light source 62 if a decontamination process is underway, or prevents activation of the light source 62 if a decontamination process is not underway at a time when the signal is transmitted by the proximity sensor 130. The light control logic 146 also controls the motor 94 to return the light source 62 to a location outside the perimeter of the display region of the computer display 14.

Figure 6:
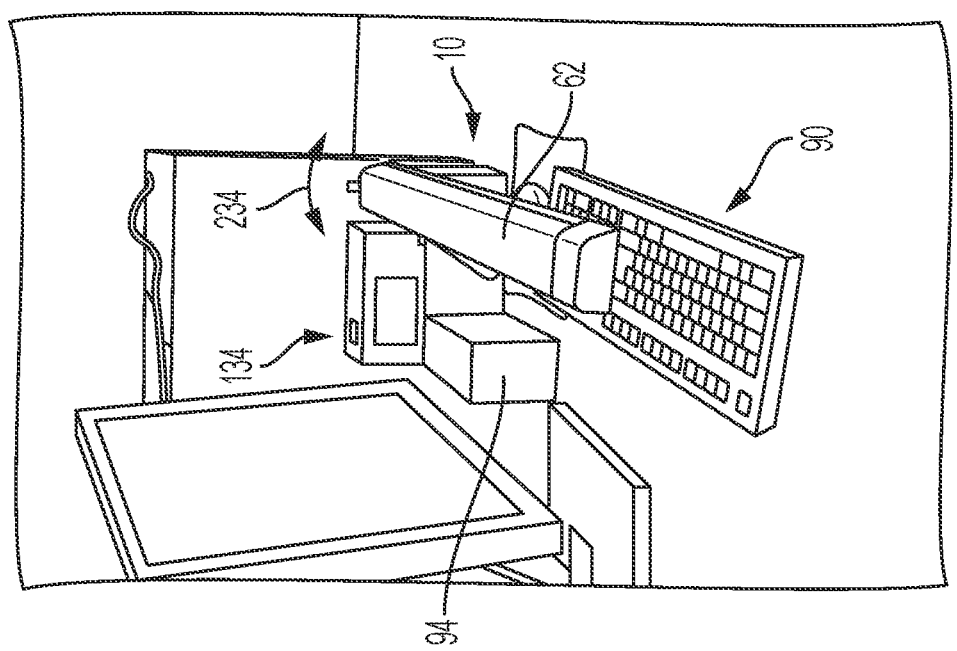
FIG. 6 is a perspective view of the decontamination apparatus of FIG. 5, with the ultraviolet light supported vertically above the keyboard in use to render exposed surfaces of the keyboard and pointing mouse pathogen reduced.
Figure 5:
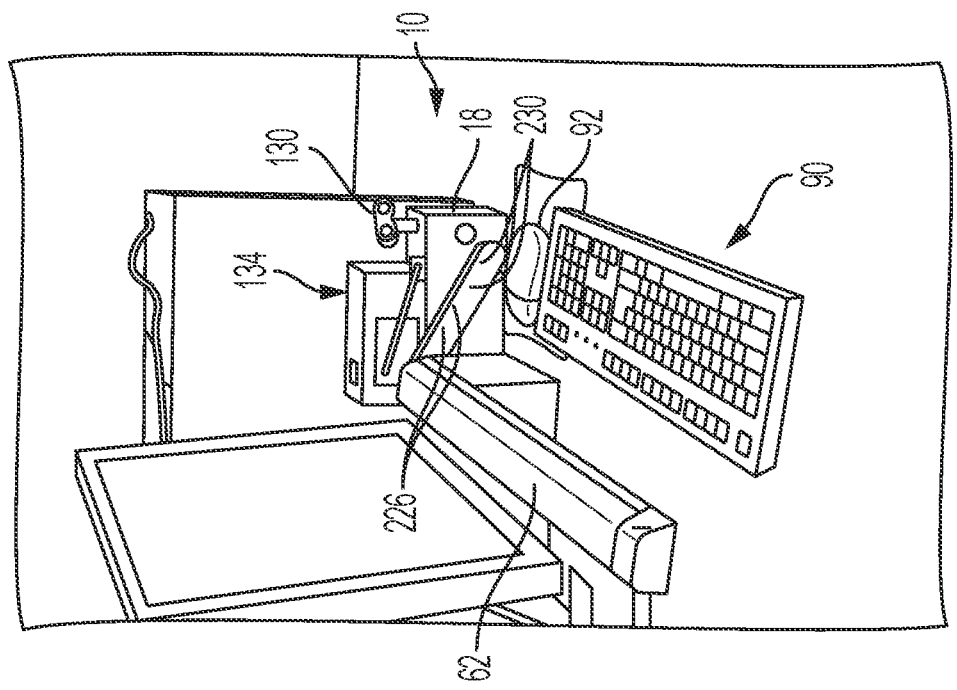
FIG. 5 is a perspective view showing another illustrative embodiment of a decontamination apparatus arranged adjacent to a computer keyboard and pointing mouse with an ultraviolet light supported in a stowed position.

The embodiment discussed above was for decontaminating a computer display 14, however, alternate embodiments of the decontamination apparatus 10 are configured to render a keyboard 90, pointing mouse 92, or other such peripheral device pathogen reduced. As shown in FIGS. 5 and 6, and similar to the previous embodiments, a frame 18 is again positioned adjacent to the objects (keyboard 90 and mouse 92) to be rendered pathogen reduced. A motor 94 (FIG. 6) and light source 62 are again operated by the controller 134, dependent upon whether a person is sensed within close proximity to the decontamination apparatus 10. But rather than moving a coupler 22 supporting the light source 62 in opposite, linear directions traversing a computer display 14, a coupler 222 comprising a pair of reciprocating arms 226 driven by a common motor is shown in FIGS. 5 and 6. Because the connection points 230 of the arms 226 to the frame 18 are laterally spaced apart in an arrangement matching the arrangement of the connection points between the arms 226 and the light source 62, as the arms are pivoted along an arcuate path indicated by arrows 234 (FIG. 6), the light source 62 orientation is maintained throughout the range of motion along the arcuate decontamination path.

It is to be noted that the phrase "at least one of", if used herein, followed by a plurality of members herein means one of the members, or a combination of more than one of the members. For example, the phrase "at least one of a first widget and a second widget" means in the present application: the first widget, the second widget, or the first widget and the second widget. Likewise, "at least one of a first widget, a second widget and a third widget" means in the present application: the first widget, the second widget, the third widget, the first widget and the second widget, the first widget and the third widget, the second widget and the third widget, or the first widget and the second widget and the third widget.

Illustrative embodiments have been described, hereinabove. It will be apparent to those skilled in the art that the above devices and methods may incorporate changes and modifications without departing from the general scope of this invention. It is intended to include all such modifications and alterations within the scope of the present invention. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A decontamination apparatus for rendering an object pathogen reduced, the decontamination apparatus comprising:
    a frame to be positioned in suitable proximity to the object to enable the decontamination apparatus to perform a decontamination process that achieves at least a predetermined minimum level of pathogen reduction on the object, wherein the frame comprises a track region along which the coupler travels to transport the light source along the decontamination path;
    a light source that emits ultraviolet light suitable to deactivate at least a portion of a pathogen population on the object;
    a coupler that receives the light source and is adjustable relative to the frame to allow the light source to be transported along a decontamination path during the decontamination process;
    a shield that interferes with transmission of the ultraviolet light in directions generally away from the object during the decontamination process;
    a controller that controls operation of the light source and transportation of the light source along the decontamination path during the decontamination process;
    a motor that is controlled by the controller; and
    a drivetrain that transmits a force generated by the motor to the coupler to transport the light source along the decontamination path, wherein the drivetrain is coupled to the frame and comprises a continuous loop of material that extends about at least a drive hub that is rotatable by the motor.

2. The decontamination apparatus of claim 1, wherein the drivetrain comprises an arm with a proximate end that cooperates with a drive shaft and a distal end that supports the light source, and rotation of the drive shaft results in rotation of the arm to transport the light source along the decontamination path.

3. The decontamination apparatus of claim 1, wherein the light source predominantly emits ultraviolet light having a wavelength within a range from approximately 10 nm to approximately 400 nm.

4. The decontamination apparatus of claim 1, wherein the shield comprises an inward-facing surface opposing the light source with an anti-reflective material that interferes with reflection of the ultraviolet light in the directions generally away from the object in a second direction generally towards the object.

5. The decontamination apparatus of claim 4, wherein the anti-reflective material provided to the inward-facing surface is a matte coating.

6. The decontamination apparatus of claim 1, wherein the light source and shield maintain a constant orientation relative to the object over an entire range of travel during the decontamination process.

7. The decontamination apparatus of claim 1, wherein the coupler comprises an arm that transports the light source along an arcuate path over the object.

8. The decontamination apparatus of claim 1, wherein the frame comprises a pair of rails separated from each other by an adjustable distance, and at least one strap that extends between the rails and about the object to secure the frame on the object between the rails.

9. The decontamination apparatus of claim 1 further comprising a sensor in communication with the controller, wherein the sensor is operable to sense a person within a defined distance from the object and communicate with the controller to cause deactivation of the light source in response to sensing the person within the defined distance.

10. The decontamination apparatus of claim 1, wherein the controller is configured to cause the light source to be transported along the decontamination path at a plurality of different velocities.

11. The decontamination apparatus of claim 10, wherein the plurality of different velocities are established by the controller in response to user input.

12. The decontamination apparatus of claim 1 further comprising a guard that interferes with transmission of the ultraviolet light from a portion of the light source, wherein the guard is supported with the light source arranged between a portion of the shield and a baffle.

13. A decontamination apparatus for rendering an object pathogen reduced, the decontamination apparatus comprising:
    a frame to be positioned in suitable proximity to the object to enable the decontamination apparatus to perform a decontamination process that achieves at least a predetermined minimum level of pathogen reduction on the object;
    a light source that emits ultraviolet light suitable to deactivate at least a portion of a pathogen population on the object;
    a coupler that receives the light source and is adjustable relative to the frame to allow the light source to be transported along a decontamination path during the decontamination process;
    a shield that interferes with transmission of the ultraviolet light in directions generally away from the object during the decontamination process, wherein the shield comprises an inward-facing surface opposing the light source with an anti-reflective material that interferes with reflection of the ultraviolet light in the directions generally away from the object in a second direction generally towards the object; and
    a controller that controls operation of the light source and transportation of the light source along the decontamination path during the decontamination process.

14. The decontamination apparatus of claim 13, wherein the frame comprises a track region along which the coupler travels to transport the light source along the decontamination path.

15. The decontamination apparatus of claim 13 further comprising a sensor in communication with the controller, wherein the sensor is operable to sense a person within a defined distance from the object and communicate with the controller to cause deactivation of the light source in response to sensing the person within the defined distance.

16. The decontamination apparatus of claim 13, further comprising:
   a motor that is controlled by the controller; and
   a drivetrain that transmits a force generated by the motor to the coupler to transport the light source along the decontamination path, wherein the drivetrain is coupled to the frame and comprises a continuous loop of material that extends about at least a drive hub that is rotatable by the motor.

17. A decontamination apparatus for rendering an object pathogen reduced, the decontamination apparatus comprising:
   a frame to be positioned in suitable proximity to the object to enable the decontamination apparatus to perform a decontamination process that achieves at least a predetermined minimum level of pathogen reduction on the object, wherein the frame comprises a pair of rails separated from each other by an adjustable distance, and at least one strap that extends between the rails and about the object to secure the frame on the object between the rails;
   a light source that emits ultraviolet light suitable to deactivate at least a portion of a pathogen population on the object;
   a coupler that receives the light source and is adjustable relative to the frame to allow the light source to be transported along a decontamination path during the decontamination process;
   a shield that interferes with transmission of the ultraviolet light in directions generally away from the object during the decontamination process; and
   a controller that controls operation of the light source and transportation of the light source along the decontamination path during the decontamination process.

18. The decontamination apparatus of claim 17, wherein the frame comprises a track region along which the coupler travels to transport the light source along the decontamination path.

19. The decontamination apparatus of claim 17 further comprising a sensor in communication with the controller, wherein the sensor is operable to sense a person within a defined distance from the object and communicate with the controller to cause deactivation of the light source in response to sensing the person within the defined distance.

20. The decontamination apparatus of claim 17, further comprising:
   a motor that is controlled by the controller; and
   a drivetrain that transmits a force generated by the motor to the coupler to transport the light source along the decontamination path, wherein the drivetrain is coupled to the frame and comprises a continuous loop of material that extends about at least a drive hub that is rotatable by the motor.

* * * * *